United States Patent
Zhu

(10) Patent No.: US 7,001,994 B2
(45) Date of Patent: Feb. 21, 2006

(54) METHODS FOR INTRODUCING MANNOSE 6-PHOSPHATE AND OTHER OLIGOSACCHARIDES ONTO GLYCOPROTEINS

(75) Inventor: Yunxiang Zhu, Framingham, MA (US)

(73) Assignee: Genzyme Corporation, Cambridge, MA (US)

( * ) Notice: Subject to any disclaimer, the term of this patent is extended or adjusted under 35 U.S.C. 154(b) by 200 days.

(21) Appl. No.: 10/051,711

(22) Filed: Jan. 17, 2002

(65) Prior Publication Data

US 2002/0137125 A1 Sep. 26, 2002

Related U.S. Application Data

(60) Provisional application No. 60/263,078, filed on Jan. 18, 2001.

(51) Int. Cl.
C12P 21/06 (2006.01)
C12N 9/36 (2006.01)

(52) U.S. Cl. ............ 536/4.1; 536/18.5; 536/18.6; 536/123.1; 536/124; 536/23.2; 536/23.5; 536/23.1; 435/68.1; 435/206; 435/195; 435/6; 435/69.1; 435/18; 435/193; 435/196; 435/208; 435/69.7; 435/97; 424/94.61; 424/155.1; 424/179.1; 424/183.1; 530/350

(58) Field of Classification Search ............ 536/4.1, 536/18.5, 18.6, 123.1, 124, 23.2, 23.5, 23.1; 435/68.1, 206, 195, 6, 69.1, 18, 193, 196, 435/208, 69.7, 97; 424/94.61, 155.1, 179.1, 424/183.1; 530/350

See application file for complete search history.

(56) References Cited

U.S. PATENT DOCUMENTS

| | | | |
|---|---|---|---|
| 6,251,858 B1 * | 6/2001 | Monsigny et al. ............ 514/8 |
| 6,534,300 B1 | 3/2003 | Canfield |
| 6,537,785 B1 | 3/2003 | Canfield |
| 6,642,038 B1 | 11/2003 | Canfield |
| 6,670,165 B1 | 12/2003 | Canfield |
| 6,770,468 B1 | 8/2004 | Canfield |
| 6,800,472 B1 | 10/2004 | Canfield et al. |
| 6,828,135 B1 | 12/2004 | Canfield |
| 6,861,242 B1 | 3/2005 | Canfield |
| 2002/0025550 A1 | 2/2002 | Canfield |
| 2002/0137125 A1 | 9/2002 | Zhu |
| 2003/0119088 A1 | 6/2003 | Canfield et al. |
| 2004/0006008 A1 | 1/2004 | Lebowitz et al. |
| 2004/0132640 A1 | 7/2004 | DeFrees et al. |
| 2005/0003486 A1 | 1/2005 | Canfield et al. |
| 2005/0026823 A1 | 2/2005 | Zankel et al. |
| 2005/0058634 A1 | 3/2005 | Zhu |

OTHER PUBLICATIONS

Tolvanen et al. "In vitro attachment of mono- and oligosaccharide to surface glycoconjugates of intact cells." The Journal of Bio Chem., vol. 261, No. 20, pp 9546-9551, 1986.*

(Continued)

Primary Examiner—James O. Wilson
Assistant Examiner—Devesh Khare
(74) Attorney, Agent, or Firm—Finnegan, Henderson, Farabow, Garrett & Dunner, LLP; Konstantin M. Linnik

(57) ABSTRACT

Methods to introduce highly phosphorylated mannopyranosyl oligosaccharide derivatives containing mannose 6-phosphate (M6P), or other oligosaccharides bearing other terminal hexoses, to carbonyl groups on oxidized glycans of glycoproteins while retaining their biological activity are described. The methods are useful for modifying glycoproteins, including those produced by recombinant protein expression systems, to increase uptake by cell surface receptor-mediated mechanisms, thus improving their therapeutic efficacy in a variety of applications.

19 Claims, 5 Drawing Sheets

OTHER PUBLICATIONS

Ashwell, Gilbert and Joe Harford. "Carbohydrate-specific Receptors of the Liver," *Ann. Rev. Biochem.*, 1982. 51, p. 531.

Kren, Betsy T., Paramita Bandyopadhyay & Clifford J. Steer. "In vivo site-directed mutagenesis of the *factor IX* gene by chimeric RNA/DNA oligonucleotides," *Nature Medicine*. Mar. 1998, vol. 4, No. 3, pp. 285-290.

Cole-Strauss, Allyson, Kyonggeun Yoon, Yufei Xiang, Bruce C. Byrne, Michael C. Rice, Jeff Gryn, William K. Holloman, Eric B. Kmiec. "Correction of the Mutation Responsible for Sickle Cell Anemia by an RNA-DNA Oligonucleotide," *Science*. Sep. 6, 1996, vol. 273, pp. 1386-1389.

Tolvanen, Martti and Carl G. Gahmberg. "In Vitro Attachment of Mono- and Oligosaccharides to Surface Glycoconjugates of Intact Cells," *The Journal of Biological Chemistry*. Jul. 15, 1986, vol. 261, No. 20, pp. 9546-9551.

Srivastava, Ohm P. and Ole Hindsgaul. "Synthesis of the 6- and 6'-Phosphates of 8-Methoxycarbonyloctyl 2-*O*-α-D-Mannopyranosyl-α-D-Mannopyranoside," *Carbohydrate Research*. 1986, No. 155, pp. 57-72.

Srivastava, Om P. and Ole Hindsgaul. "Synthesis of Phosphorylated Trimannosides Corresponding to End Groups of the High-mannose Chains of Lysosomal Enzymes," *Carbohydrate Research*. 1987, No. 161, pp. 195-210.

Srivastava, Om P. and Ole Hindsgaul. "Synthesis of Phosphorylated Pentasaccharides Found on Asparagine-Linked Carbohydrate Chains of Lysosomal Enzymes," *Journal of Organic Chemistry*. 1987, No. 52, pp. 2869-2875.

Srivastava, Om P. and Ole Hindsgaul. "Synthesis if 6'-*O*-phosphorylated *O*-α-D-mannopyranosyl-(1→6)-α-D-mannopyranosides," *Carbohydrate Research*. 1987, No. 161, pp. 324-329.

Braslawsky, Gary R., Kathleen Kadow, Jay Knipe, Kerry McGoff, Mary Edson, Takushi Kaneko, and Robert S. Greenfield. "Adriamycin (hydrazone)-antibody conjugates require internalization and intracellular acid hydrolysis for antitumor activity," *Cancer Immunol Immunother*. 1991, No. 33, pp. 367-374.

Bayer, Edward A., Haya Ben-Hur, and Meir Wilchek. "Biocytin Hydrazide—A Selective Label for Sialic Acids, Galactose, and Other Sugars in Glycoconugates Using Avidin-Biotin Technology," *Analytical Bioichemistry*. 1988, No. 170, pp. 271-281.

O'Shannessy, Daniel J. and Richard H. Quarles. "Specific Conjugation Reactions of the Oligosaccharide Moieties of Immunoglobulins," *Journal of Applied Biochemistry*. 1985, No. 7, pp. 347-355.

Kralovec, J., M. Singh, M. Mammen, A. H. Blair, and T. Ghose. "Synthesis of site-specific methotrexate-lgG conjugates: Comparison of stability and antitumor activity with active-ester-based conjugates," *Cancer Immunol Immunother*. 1989, No. 29, pp. 293-302.

Distler, Jack J., Jinfeng Guo, George W. Jourdian, Om P. Srivastava, and Ole Hindsgaul. "The Binding Specificity of High and Low Molecular Weight Phosphomannosyl Receptors from Bovine Testes: Inhibition Studies with Chemically Synthesized 6-*O*-phosphorylated Oligomannosides," *The Journal of Biological Chemistry*. Nov. 15, 1991, vol. 266, No. 22, pp. 21687-21692.

Gahmberg, Carl G. and Martti Tolvanen. "Nonmetabolic Radiolabeling and Tagging of Glycoconjugates," *Methods in Enzymology*. 1994, vol. 230, pp. 32-45.

Wilchek, Meir and Edward A. Bayer. "Labeling Glycoconjugates with Hydrazide Reagents," *Methods in Enzymology*. 1987, vol. 138, pp. 429-442.

Slodki, M. E. "Phosphate Linkages in Phosphomannans from Yeast," *Biochimica et Biophysica Acta*. 1962, No. 57, pp 525-533.

Bretthauer, R. K., G. J. Kaczorowski, and M. J. Weise. "Characterization of a Phosphorylated Pentasaccharide Isolated from *Hansenula holstii* NRRL Y-2448 Phosphomannan," *Biochemistry*. 1973, vol. 12, No. 7, pp. 1251-1256.

Baba, Tadashi, Ken Watanabe, Naoko Yonezawa, Misao Hiroto, and Yuji Arai. "Preparation and Application of a Pentamannosyl Monophosphate-Bovine Serum Albumin Conjugate," *Carbohydrate Research*. 1988, No. 177, pp. 163-172.

Bándyopadhyay, Paramita, Xiaoming Ma, Cheryle Linehan-Stieers, Betsy T. Kren, and Clifford J. Steer. "Nucleotide Exhange in Genomic DNA of Rat Hepatocytes Using RNA/DNA Oligonucleotides," *The Journal of Biological Chemistry*. Apr. 9, 1999, vol. 274, No. 15, pp. 10163-10172.

Ioannou, Yiannis A., David F. Bishop, and Robert J. Desnick. "Overexpression of Human α-Gálactosidase A Results in Its Intracellular Aggregation, Crystallization in Lysosomes, and Selective Secretion," *The Journal of Cell Biology*. Dec. 1992, vol. 119, No. 5, pp. 1137-1150.

Matsuura, Fumito, Masaua Ohta, Yiannis A. Ioannou, and Robert J. Desnick. "Human α-galactosidase A: characterization of the *N*-linked oligosaccharides on the intracellular and secreted glycoforms overexpressed by Chinese hamster ovary cells," *Glycobiology*. 1998, vol. 8, No. 4, pp. 329-339.

Zhao, Ke-Wei and Elizabeth F. Neufeld. "Purification and Characterization of Recombinant Human α-*N*-Acetylglucosaminidase Secreted by Chinese Hamster Ovary Cells," *Protein Expression and Purification*. 2000, No. 19, pp. 202-211.

Kornfeld, Stuart and Ira Mellman. "The Biogenesis of Lysosomes," *Annu. Rev. Cell Biology*. 1989, No. 5, pp. 483-525.

Tong, Patrick Y., Walter Gregory, and Stuart Kornfeld. "Ligand Interactions of the Cation-independent Mannose 6-Phosphate Receptor," *The Journal of Biological Chemistry*. May 15, 1989, vol. 264, No. 14, pp. 7962-7969.

Yoon, Kyonggeun, Allyson Cole-Strauss, and Eric B. Kmiec. "Targeted gene correction of episomal DNA in mammalian cells mediated by a chimeric RNA-DNA oligonucleotide," *Proc. Natl. Acad. Sci. USA*. Mar. 1996, vol. 93, pp. 2071-2076.

Rando, Thomas A., Marie-Helene Disatnik, and Lucy Z.-H. Zhou. "Rescue of dystrophin expression in *mdx* mouse muscle by RNA/DNA oligonucleotides," *PNAS*. May 9, 2000, vol. 97, No. 10, pp. 5363-5368.

Kren, Betsy T., Bhupesh Parashar, Paramita Bandyopadhyay, Namita Roy Chowdhury, Jaynata Roy Chowdhury, and Clifford J. Steer. "Correction of the UDP-glucuronosyltransferase gene defect in the Gunn rat model of Crigler-Najjar Syndrome type I with a chimeric oligonucleotide," *Proc. Natl. Acad. Sci. USA*. Aug. 1999, vol. 96, pp. 10349-10354.

Bijvoet, Agnes G. A., Hans Van Hirtum, Marian A. Kroos, Esther H. M. Van de Kamp, Onard Schoneveld, Pim Visser, Just P. J. Brakenhoff, Miranda Weggeman, Emile J. van Corven, Ans T. Van der Ploeg, and Arnold J. J. Reuser. "Human acid α-glucosidase from rabbit milk has therapeutic effect in mice with glycogen storage disease type II," *Human Molecular Genetics*. 1999, vol. 8, No. 12, pp. 2145-2153.

Tomoda, Hiroshi, Yukihide Ohsumi, Yoshitaka Ichikawa, Om P. Srivastava, Yasuo Kishimoto, and Yuan Chuan Lee. "Binding specificity of D-mannose 6-phosphate receptor of rabbit alveolar macrophages," *Carbohydrate Research.* 1991, vol. 213, pp. 37-46.

Molema, Grietje, Robert W. Jansen, Jan Visser, Piet Herdewijn, Frits Moolenaar, and Dirk K. F. Meijer. "Neoglycoproteins as Carriers for Antiviral Drugs: Synthesis of Analysis of Protein-Drug Conjugates," *J. Med. Chem.* 1991, vol. 34, pp. 1137-1141.

Kakkis, Emil D., Anna Matynia, Adam J. Jonas, and Elizabeth F. Neufeld. "Overexpression of the Human Lysosomal Enzyme α-L-Iduronidase in Chinese Hamster Ovary Cells," *Protein Expression and Purification.* 1994, No. 5, pp. 225-232.

Amalfitano et al., "Systemic Correction of the Muscle Disorder Glycogen Storage Disease Type II After Hepatic Targeting of a Modified Adenovirus Vector Encoding Human Acid-α-Glucosidase," *Proc. Natl. Acad. Sci. USA.* 96:8861-8866 (1999).

Arakatsu et al., "V. Specificity and Cross-Reactivity with Dextrans of the Antibodies Formed in Rabbits to Isomaltonic and Isomaltotrionic Acids Coupled to Bovine Serum Albumin," Immunochemical Studies on Dextrans, The Journal of Imunology, vol. 97, No. 8 (1966).

Bernstein et al., "A general synthesis of model glycoproteins: coupling of alkenyl glycosides to proteins, using reductive oxonolysis followed by reductive amination with sodium cyanoborohydride," Carbohydrate Research, vol. 78, C1-C3 (1980).

Bijvoet et al., "Generalized Glycogen Storage and Cardiomegaly in a Knockout Mouse Model of Pompe Disease," Human Molecular Genetics, vol. 7 No. 1 (1998).

Chaudhari et al., Coupling of Amino Acids and Amino Sugars with Cyanuric Chloride (2,4,6-Trichloro-s-triazine), Can. J. Chem., vol. 50, No. 13 (1972).

Chen et al., "Towards a Molecular Therapy for Glycogen Storage Disease Type II (Pompe Disease))," Molecular Medicine Today, vol. 6, Issue 6, pp. 245-251 (2000).

Davis, "Recent Developments in Glycoconjugates," J. Chem. Soc., vol. 1, pp. 3215-3237 (1999).

Davis, "Synthesis of Glycoproteins," Chem. Rev., vol. 102, pp. 579-601 (2002).

Davis et al., "Glycoprotein Stythesis: From Glycobiological Tools to Tailor-Made Catalysts," Synlett 9:1495-1507 (1999).

Fielder et al., "An Immunogenic Polysaccharide-Protein Conjugate," J. Immunol., vol. 105, No. 1 (1970).

Furbish et al., "Uptake and Distribution of Placental Glucocerebrosidase in Rat Hepatic Cells and Effects of Sequential Deglycosylation," Biochim. Biophys. Acta, vol. 673, pp. 425-434 (1981).

Gray, "The Direct Coupling of Oligosaccharides to Proteins and Derivatized Gels," Archives of Biochemistry and Biophysics, vol. 163, pp. 426-428 (1974).

Helenius et al., "Intracellular Functions of N-Linked Glycans," Science Magazine, vol. 291 (2001).

Himmelspach et al., "Use of 1-(m-aminophenyl)flavazoles for the preparation of immunogens with oligosaccharide determinant groups," Eur. J. Immunol., vol. 106, No. 1 (1971).

King et al., "Preparation of Protein Conjugates via Intermolecular Hydrazone Linkage," Biochemistry 25: 5774-5779 (1986).

Kleinhammer et al., "Synthesis and immunological properties of an artificial antigen with the repeating oligosaccharide unit of *Salmonella illinois* as haptenic group," Eur. J. Immunol., vol. 3, pp. 834-838 (1973).

Lee et al., "2-Imino-2-Methoxyethyl 1-Thioglycosides: New Reagents for Attaching Sugars to Proteins," Biochemistry 15:3956-3963 (1976).

Lee et al., "A Biochemical and Pharmacological Comparison of Enzyme Replacement Therapies for the Glycolipid Storage Disorder Fabry Disease," Glycobiology vol. 13, No. 4, pp. 305-313 (2003).

Lemieux et al., "The Properties of a "Synthetic" Antigen Related to the Human Blood-Group Lewis a," J. of the American Chem. Society, pp. 4076-4083 (1975).

Li et al., "Isolation and Characterization of Mannose 6-Phosphate/Insulin-Line Growth Factor II Receptor from Bovine Serum," *Glycobiol.*, 1:511-517 (1991).

Matsuura et al., "Human a-galactosidase A: characterization of the *N*-linked oligosaccharides on the intracellular and secreted glycoforms overexpressed by Chinese hamster ovary cells," Glycobiology vol. 8 No. 4, pp. 329-339 (1998).

Mcbroom et al., "Carbohydrate Antigens: Coupling of Carbohydrates to Proteins by Diazonium and Phenylisothiocyanate Reactions," Methods in Enzymology vol. XXVII, Complete Carbohydrates, Part B 212-222 (1972).

Moczar et al., "Preparation of *N*-Acetylglucosamine Derivatives of Proteins," FEBS Letters vol. 50 No. 3 (1975).

Montalvo et al., "Glycogenesis type II: identification and expression of three novel mutations in the acid a-glucosidase gene causing the infantile form of the disease," Elsevier Inc., Molecular Genetics and Metabolism 81, pp. 203-208 (2004).

Moreland et al., "Lysosomal Acid a-Glucosidase Consists of Four Different Peptides Processed from a Single Chain Precursor," J. Biol. Chem., vol. 280 No. 8, pp. 6780-6791 (2005).

Orr et al., "Synthetic Concanavalin A Receptors and Erythrocyte Agglutination," Nature 272:722-725 (1978).

Raben et al., "Enzyme Replacement Therapy in the Mouse Model of Pompe Disease," Molecular Genetics and Metabolism vol. 80, pp. 159-169 (2003).

Raben et al., "Glycogen Stored in Skeletal but Not in Cardiac Muscle in Acid α-Glucosidase Mutant (Pompe) Mice is Highly Resistant to Transgene-Encoded Human Enzyme," *Mol. Ther.*, 6:601-608 (2002).

Raben et al., "Replacing Acid a-Glucosidase in Pompe Disease: Recombinant and Transgenic Enzymes are Equipotent, but Neither Completely Clears Glycogen from Type II Muscle Fibers," Molecular Therapy vol. 11, No. 1 (2005).

Raben et al., "Targeted Disruption of the Acid α-Glucosidase Gene in Mice Causes and Illness with Critical Features of Both Infantile and Adult Human Glycogen Storage Disease Type II," *J. Biol. Chem.*, 273:19086-19092 (1998).

Reuser et al., "Uptake and Stability of Human and Bovine Acid a-Glucosidase in Cultured Fibroblasts and Skeletal Muscle Cells from Glycogenosis Type II Patients," Experimental Cell Research, vol. 155, Issue 1, pp. 178-189 (1984).

Rodwell et al., "Site-specific covalent modification of monoclonal antibodies: In vitro and in vivo evaluations," Proc. Natl. Acad. Sci. USA, vol. 83, pp. 2632-2636 (1986).

Schwartz et al., "Preparation of Hydrazino-Modified Proteins and Their Use for the Synthesis of $^{99m}$Tc-Protein Conjugates," Bioconjugate Chem., vol. 2, pp. 333-336 (1991).

Sears et al., "Toward Automated Synthesis of Oligosaccharides and Glycoproteins," Science vol. 291 (2001).

Tang et al., "Novel Approach to the Study of the Antigenicities and Receptor Functions of Carbohydrate Chains of Glycoproteins," Biochemical and Biophysical Research Communications 132:474-480 (1985).

Townsend et al., "Analysis of Glycoprotein Oligosaccharides Using High-pH Anion Exchange Chromatography," *Glycobiol.*, 1:139-147 (1991).

Valenzano et al., "Soluble Insulin-Like Growth Factor II/ Mannose 6-Phosphate Receptor Carries Multiple High Molecular Weight Forms of Insulin-Like Growth Factor II in Fetal Bovine Serum," J. Biol. Chem., 270:16441-16448 (1995).

Van Hove et al., "High-Level Production of Recombinant Human Lysosomal Acid a-Glucosidase in Chinese Hamster Ovary Cells Which Targets to Heart Muscle and Corrects Glycogen Accumulation in Fibroblasts from Patients with Pompe Disease," *Proc. Natl. Acad. Sci USA*, 93:65-70 (1996).

Varki et al., "Structural Studies of Phosphorylated High Mannose-Type Oligosaccharides," *J. Biol. Chem.*, 255: 10847-10858 (1980).

Wadhwa et al., "Receptor Mediated Glycotargeting," J. Drug Targeting, vol. 11 (5), pp. 255-268 (2003).

Yamazaki et al., "Endogenous Lectins as Targets for Drug Delivery," Advanced Drug Delivery Reviews vol. 43, pp. 225-244 (2000).

Zhang et al., "Linking Carbohydrates to Proteins Using N-(2,2-Dimethoxyethyl)-6-hydroxy Hexanamide," Tetrahedron vol. 54, pp. 11783-11792 (1998).

Zhao et al., "Purification and Characterization of Recombinant Human α-N-Acetylglucominidase Secreted by Chinese Hamster Ovary Cells," Protein Expression and Purification, vol. 19, pp. 202-211 (2000).

Zhou et al., "Mannose 6-Phosphate Quantitation in Glycoproteins Using High-pH Anion-Exchange Chromatography with Pulsed Amperometric Detection," *Anal. Biochem.*, 306:163-170 (2002).

Zhu et al., "Carbohydrate-remodeled acid *a*-glucosidase with higher affinity for the cation-independent mannose 6-phosphate receptor demonstates improved delivery to muscles of Pompe mice," Biochemical Journal Immediate Publication (2005).

Zhu et al., "Conjugation of Mannose 6-Phosphate-containing Oligosaccharides to Acid α-Glucosidase Improves the Clearance of Glycogen in Pompe Mice," The Journal of Biological Chemistry, vol. 279, No. 48, pp. 50336-50341 (2004).

* cited by examiner

METHODS FOR INTRODUCING MANNOSE 6-PHOSPHATE AND OTHER OLIGOSACCHARIDES ONTO GLYCOPROTEINS

This application hereby claims the benefit of U.S. provisional patent application No. 60/263,078, filed Jan. 18, 2001, which is herein incorporated by reference in its entirety.

BACKGROUND OF THE INVENTION

The present invention relates in general to methods for introducing new oligosaccharides to glycoproteins, and more specifically, to novel methods for conjugating highly phosphorylated mannopyranosyl oligosaccharide derivatives to glycoproteins to form compounds containing mannose-6-phosphate (M6P) for use in medical methods of treatment, and to the compounds thereby produced.

Carbohydrates on glycoproteins play important biological functions in bio-organisms. Well-characterized examples include the selectin-carbohydrate interaction involved in intercellular cell adhesion and sperm/egg interaction (see, e.g., C. G. Gahmberg et al., 27 APMIS SUPPL. 39, (1992)), and the mannose 6-phosphate (M6P) dependent lysosomal enzyme targeting pathway (see, e.g., S. Kornfeld and I. Mellman, 5 ANNUAL REVIEW OF CELL BIOLOGY 483 (1989)). To facilitate study of the complex functions of carbohydrate structures on glycoproteins, both enzymatic and chemical methods have been developed to remove the carbohydrate glycans from glycoproteins for analysis. A variety of conjugation methods have also been developed to conjugate defined carbohydrates to proteins and then analyze their possible biological functions. The most commonly used conjugation approach involves the use of omega-amino groups of lysine residues. Reactions of amino groups of proteins with compounds such as N-hydroxysuccinimide ester or isothiocyanate derivatives are widely used. Reductive amination, on the other hand, is most commonly used for carbohydrate conjugation to proteins. For example, in the analysis of lysosomal enzyme targeting, coupling of M6P or phosphopentamannose to bovine serum albumin has been achieved through reductive amination (H. Tomoda et al., 213 CARBOHYDR. RES. 37 (1991); T. Baba et al., 177 CARBOHYDR. RES. 163 (1988)), leading to significant insights regarding the M6P receptor binding to lysosomal enzymes through these M6P conjugated glycoproteins. Reductive amination involves covalently linking the reducing ends of oligosaccharides to amino acid residues in proteins containing free amines (such as lysines), to first form unstable Schiff bases which are then reduced by cyanoborohydride to stable imine bonds.

However, these known conjugation methods are limited in that they are not specific in terms of the amino acid residues involved, and require the direct linkage of chemical conjugates or carbohydrates to amino acid residues, which may cause a change in protein conformation and destroy the biological activity of proteins. For example, when antibody IgG is coupled to various chemical conjugates through amino acid groups, the antibody IgG often loses its immunological activity (D. J. O'Shannessy and R. H. Quarles, 7 J. OF APPL. BIOCHEM. 347, (1985); T. I. Ghose et al., 93 METHODS IN ENZYMOLOGY 280 (1983)). In addition, reductive amination requires high pH and a reductive reagent that may also reduce any disulfide bonds in a protein, thus potentially destroying biological activity.

A more specific approach to introduce certain chemical conjugates onto glycoproteins has been described and involves covalent bond formation between carbonyl (aldehyde) groups generated by mild oxidation of carbohydrates with periodate or galactose oxidase (G. Avigad et al., 237 J. BIOL. CHEM. 2736(1962)) and chemical compounds containing carbonyl-reactive groups. This approach has been used for in vitro attachment of mono- and oligosacharides to cell surface glycoconjugates of living cells with glycosylhydrazines (M. Tolvanen and C. G. Gahmberg, 261(2) J. BIOL. CHEM. 9546 (1986); C. G. Gahmberg and M. Tolvanen, 230 METHODS IN ENZYMOLOGY 32 (1994)). Other applications include conjugation of biotin or avidin to glycoproteins with biotin-hydrazide or avidin-hydrazide (Bayer et al., 161 ANALYTICAL BIOCHEMISTRY 123 (1987); Bayer et al., 170 ANALYTICAL BIOCHEMISTRY 271 (1988); M. Wilchek and E. A. Bayer, 128 METHODS IN ENZYMOLOGY 429 (1987)), antibody IgG conjugation for immunodetection (O'Shannessy et al., 8 IMMUNOLOGY LETTERS 273 (1984); (D. J. O'Shannessy and R. H. Quarles, 7 J. OF APPL. BIOCHEM. 347, (1985)) and cancer immunotherapy (J. Singh Kralovec et al., 29 CANCER IMMUNOLOGY THERAPY 293 (1989); G. R. Braslawsky et al., 33 CANCER IMMUNOLOGY THERAPY 367 (1991)). In these examples, the glycoproteins are treated by mild oxidation with periodate to generate aldehyde groups that then react with hydrazide derivatives. One advantage of this approach for conjugation is that the linkage is through the carbohydrates on the glycoproteins instead of directly involving the protein backbone, thus avoiding inactivation of the glycoproteins' biological activity. Antibodies modified in such a way always retain activity (D. J. O'Shannessy et al., 8 IMMUNOLOGY LETTERS 273 (1984); D. J. O'Shannessy and R. H. Quarles, 7 J. OF APPL. BIOCHEM. 347, (1985)). In addition, both the oxidation and the covalent bond formation steps are nearly quantitative, and reaction conditions are very mild, thus helping retain the biological activity of the proteins. Retention of biological activity is critical when the modified glycoproteins are to be used for therapeutic purposes.

Lysosomal storage disease describes a class of over 40 genetic disorders (see, e.g., HOLTON, J. B., THE INHERITED METABOLIC DISEASES 205–242 ($2^{nd}$ ed. 1994); SCRIVER ET AL., 2 THE METABOLIC BASIS OF INHERITED DISEASE ($7^{th}$ ed. 1995)), each resulting from a deficiency of a particular lysosomal enzyme, usually as a result of genetic mutation. Lysosomal enzymes are required to break down protein, glycolipid and carbohydrate metabolites within the lysosomes of cells. When one or more of these enzymes are defective in affected individuals due to inherited mutations, lysosomes in cells of affected individuals accumulate a subset of undigested substrates, largely liposaccharides and carbohydrates as storage materials that are unable to be digested by the defective enzymes. For example, in Gaucher disease, deficiency of beta-glucocerebrosidase causes the accumulation of glucosylceramide; in Fabry disease, the defective alpha-galactosidase A results in accumulation of globotriaosylceremide; in Pompe disease, lack of acid alpha-glucosidase causes accumulation of glycogen alpha 1–4 linked oligosaccharides and in Tay-Sachs disease, deficiency of beta-N-acetyl-hexosaminidase leads to accumulation of GM2 ganglioside. Clinically, patients with these syndromes show a variety of symptoms associated with the accumulation of these storage material in the lysosomes, which eventually affect the normal function of the cells or tissues that result in dysfunction of organs within the human body. The severity of the disease varies with the residual enzyme activity, in severe cases, death can occur early in life.

Lysosomal enzymes, like other secretory proteins, are synthesized and co-translationally translocated into the lumen of the endoplasmic reticulum, where post-translational carbohydrate modification occurs. However, while in transit through the Golgi, they are segregated from the other secretory proteins by specifically acquiring the M6P recognition marker generated by the sequential actions of two enzymes. The first enzyme, UDP-N-acetylglucosamine:Lysosomal-enzyme N-Acetylglucosamine-1-phosphotransferase, transfers the N-acetylglucosamine-1-phosphate to one or more mannose residues on lysosomal enzymes to give rise to phophodiester intermediates, and the second enzyme, N-acetylglucosamine-1-phosphodiester alpha-N-acetylglucosaminidase, removes the N-acetylglucosamine from the phosphodiester to expose the M6P. Once the lysosomal enzymes with the M6P recognition marker reach the trans-Golgi-network, they are recognized by two specific receptors, the cation-independent mannose 6-phosphate receptor (CI-MPR) and the cation-dependent mannose 6-phosphate receptor (CD-MPR). These receptors with their ligands of lysosomal enzymes are sequestered into clathrin-coated vesicles formed on the trans-Golgi network and transported to endosomes, where the lysosomal enzymes are dissociated from the receptors by the low pH in endosomes and eventually delivered to lysosomes. Some of the lysosomal enzymes are secreted, however, they are captured by binding to the CI-MPR on the cell surface and internalized by the AP-2 mediated clathrin-coated vesicles. Thus, the M6P dependent pathway is the main targeting pathway for lysosomal enzymes, though the M6P independent targeting pathway has been proposed for a few lysosomal enzymes and in certain cell types (see Kornfeld and Mellman, supra).

With the complete elucidation of the lysosomal enzyme targeting pathway and the discovery of lysosomal enzyme deficiencies as the primary cause of lysosomal storage diseases, attempts have been made to treat patients having lysosomal storage diseases by intravenous administration of the missing enzyme, i.e., enzyme replacement therapy, where the injected enzymes are expected to be taken up by target cells through receptor-mediated endocytosis and delivered to lysosomes. Animal models and some clinical trials of enzyme replacement therapy have offered positive results. However, for lysosomal diseases other than Gaucher disease, some evidence suggest that enzyme replacement therapy is most effective when the enzyme being administered has M6P, so that the enzymes can be taken up efficiently by the target cells through the cell surface associated CI-MPR-mediated endocytosis. Gaucher disease, caused by the deficiency of beta-glucocerebrosidase, is an exception because beta-glucocerebrosidase is among the few lysosomal enzymes that are targeted by the M6P independent pathway (see Kornfeld and Mellman, supra). Targeting of beta-glucocerebrosidase for Gaucher disease enzyme replacement therapy to macrophage cells is mediated by remodeling its carbohydrate to expose the core mannose, which binds to the mannose receptor on macrophage cell surface.

While enzyme replacement therapy appears promising, supplies of the required enzymes are limited. Lysosomal enzymes can, in theory, be isolated from natural sources such as human placenta or other animal tissues. However, large-scale production of sufficient quantities of enzymes for therapeutic administration is difficult. Further, due to the degradation of carbohydrates in lysosomes, enzymes purified from tissues do not contain significant amounts of M6P. Alternative approaches include use of recombinant protein expression systems, facilitated by large-scale cell culture or fermentation. For example, lysosomal enzymes have been expressed in Chinese hamster ovary (CHO) cells (V. A. Ioannou et al., 119(5) J. CELL BIOL. 1137 (1992); E. D. Kakkis et al., 5 PROTEIN EXPRESSION PURIFICATION 225 (1994)), insect cells (Y. Chen et al., 20(2) PROTEIN EXPR. PURIF. 228, (2000)), and in transgenic animals or plants (A. G. Bijvoet et al., 8(12) HUM. MOL. GENET. 2145 (1999)). However, lysosomal enzymes purified from recombinant expression systems are also often not well phosphorylated and the extent of M6P phosphorylation varies considerably with different enzymes. Alpha-galactosidase A expressed in CHO cells contains about 20% of phosphorylated enzymes, but only 5% are bisphosphorylated, which is the high-uptake form (F. Matsuura et al., 8(4) GLYCOBIOLOGY 329 (1998)). Alpha-N-acetylglucosaminidase expressed in CHO cells is almost completely lacking M6P phosphorylation (K. Zhao and E. F. Neufeld, 19 PROTEIN EXPR. PURIF. 202 (2000)). In addition, recombinant proteins expressed in plants, insect cells or the methotrophic yeast *pichia pastoris* do not have any M6P phosphorylation because such cells do not have the M6P targeting pathway.

Lysosomal enzymes lacking in M6P phosphorylation compete poorly for receptor-mediated endocytic uptake by target cells and are thus of limited efficacy in enzyme replacement therapy. More specifically, poorly phosphorylated enzymes are effectively removed by the mannose receptor (M. E. Taylor et al., 252 AM. J. PHYSIOL. E690 (1987)) and asiologlycoprotein receptor in liver (Ashwell and Harford, 51 ANN. REV. BIOCHEM 531 (1982)), which can remove most of any administered lysosomal enzymes within a very short period of time.

Against this background, a strong need exists for improved, efficient approaches to phosphorylate lysosomal enzymes, and particularly for methods to modify lysosomal enzymes with M6P. In addition, a need exists for modifying lysosomal enzymes to a high-uptake, bisphosphorylated form. Such modified enzymes would be particularly useful for enhancing the efficacy of enzyme replacement therapy for lysosomal storage disease.

BRIEF SUMMARY OF THE INVENTION

Methods of creating neoglycoproteins are provided that increase the cellular uptake of lysosomal enzymes and other glycoproteins by covalently attaching oligosaccharide compositions to oxidized glycans of the glycoproteins through covalent bonds.

Thus, in one embodiment, the present invention is directed toward a method for coupling a highly phosphorylated mannopyranosyl oligosaccharide compound to a glycoprotein having at least one glycan, the method comprising derivatizing the highly phosphorylated manopyrosanyl oligosaccharide compound with a chemical compound containing a carbonyl-reactive group; oxidizing the glycoprotein having the at least one glycan to generate at least one aldehyde group on the glycoprotein; and reacting the oxidized glycoprotein having at least one glycan with the derivatized highly phosphorylated mannopyranosyl oligosaccharide compound to form a new compound having a hydrazone bond. The glycoprotein in one embodiment is a lysosomal enzyme.

In one embodiment of the methods, the highly phosphorylated mannopyranosyl oligosaccharide compound contains at least one mannose 6-phosphate group, such as a compound having the formula 6-P-$M_n$-R wherein:

M is a mannose or mannopyranosyl group;

P is a phosphate group linked to the C-6 position of M;

R comprises a chemical group containing at least one carbonyl-reactive group; and n is an integer from 1–15, wherein if n>1, $M_n$ are linked to one another by alpha (1,2), alpha (1,3), alpha (1,4), or alpha (1,6). Thus, the highly phosphorylated mannopyranosyl oligosaccharide compound includes compounds such as M6P, phosphopentamannose derived from Hansenula holstii O-phosphomannan, and 6-P-M-(alpha 1,2)-M(alpha 1,2)-M.

In another embodiment of the methods, the highly phosphorylated mannopyranosyl oligosaccharide compound comprises a compound having the formula $(6-P-M_x)_m L_n-R$ wherein:

M is a mannose or mannopyranosyl group;
L is a mannose or other hexose or other chemical groups;
P is a phosphate group linked to the C-6 position of M;
R comprises a chemical group containing at least one carbonyl-reactive group;
m is an integer from 2–3;
n is an integer from 1–15, wherein if n>1, $L_n$ are linked to one another by alpha (1,2), alpha (1,3), alpha (1,4), or alpha (1,6); and
x is an integer from 1–15. Thus, the highly phosphorylated mannopyranosyl oligosaccharide compound includes biantennary mannopyranosyl oligosaccharide compounds containing bis-M6P and triantennary mannopyranosyl oligosaccharide compounds containing bis-M6P or tri-M6P.

In one embodiment of the methods, the highly phosphorylated mannopyranosyl oligosaccharide compound can be replaced with other oligosaccharide compositions containing terminal hexoses, such as, for example, a galactose, a mannose, N-acetylglucosamine, or a fucose, which can bind to different carbohydrate-binding receptors other than CI-MPR.

In another embodiment of the methods, the chemical compound containing carbonyl-reactive group includes any compound that reacts with carbonyl groups to form a hydrazone bond. Such compounds include hydrazines, hydrazides, aminooxy, and semicarbazides and the like.

In addition, the methods further encompass reducing the compound having a hydrazone bond with a reducing agent such as cyanoborohydride to form a compound having an imine bond.

The invention is further directed toward chemical compounds produced by coupling a first chemical compound having at least one carbonyl group (aldehyde or ketone) to a second chemical compound comprising a phosphorylated mannopyranosyl oligosaccharide derivative, according to the coupling methods described and herein, i.e. by derivatizing the highly phosphorylated manopyrosanyl oligosaccharide compound with a chemical compound containing a carbonyl-reactive group; and reacting to the first chemical compound having at least one carbonyl group with the derivatized highly phosphorylated mannopyranosyl oligosaccharide compound to form a new compound having a hydrazone bond. Such compounds include antiviral compounds and gene targeting delivery agents.

In another embodiment, the invention is directed toward methods of treating lysosomal storage disease in a subject in need thereof, the methods including administering to the subject an effective amount of a glycoprotein coupled according to the methods described herein to a second chemical compound comprising a highly phosphorylated mannopyranosyl oligosaccharide derivative containing at least one mannose 6-phosphate group. Lysosomal storage diseases that are treated with a glycoprotein modified according to the methods described herein include Fabry disease, Pompe disease, and others (for a complete list, see J. B. HOLTON, THE INHERITED METABOLIC DISEASES 205–242 (2d ed. 1994); C. R. SCRIVER ET AL., 1995, 2 THE METABOLIC BASIS OF INHERITED DISEASE ($7^{th}$ ed. 1995)).

The present methods couple highly phosphorylated mannopyranosyl oligosaccharides containing M6P, to glycoproteins, so that cellular uptake of such glycopropteins is enhanced without destroying their biological activity. As such, the methods and compounds produced thereby are especially useful where in medical treatment methods that benefit from enhanced uptake forms of glycoproteins, such as in enzyme replacement therapy for the treatment of lysosomal storage diseases.

DETAILED DESCRIPTION OF THE INVENTION

Figure 1:
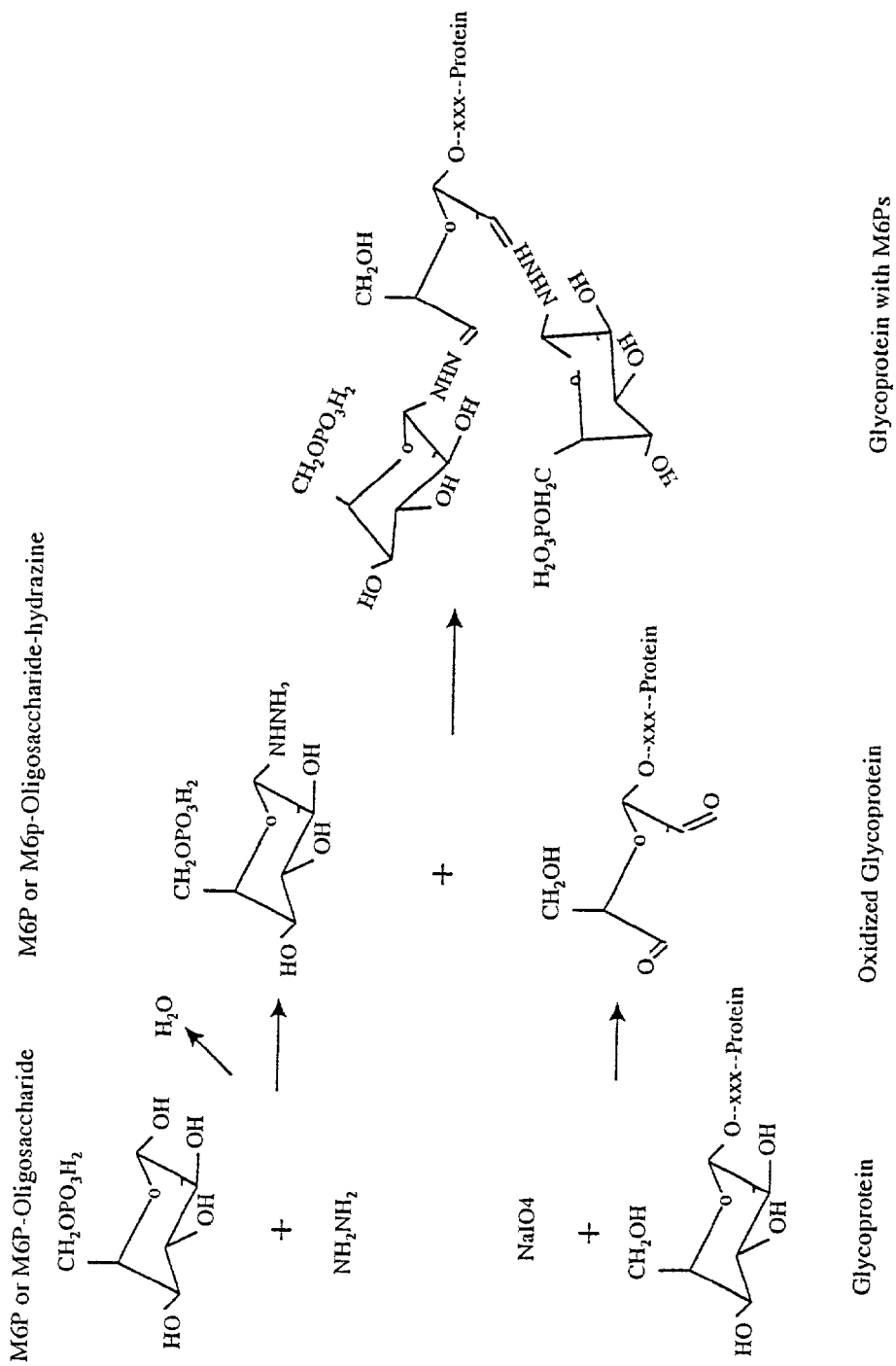
FIG. 1 is a schematic representation of the conjugation methods.

The present methods couple highly phosphorylated mannopyranosyl oligosaccharides containing M6P to glycoproteins, such as, for example, avidin and lysosomal enzyme beta-glucuronidase, without destroying biological activity. The present methods thus provide a novel approach to introduce highly phosphorylated mannosyloligosaccharide derivatives to lysosomal enzymes and other glycoproteins. In exemplary embodiments, the methods and compounds described herein are useful for modifying lysosomal enzymes produced by recombinant protein expression system with M6P, thus to enhance the efficacy of enzyme replacement therapy of lysosomal storage diseases As used herein, the term "highly phosphorylated" refers to a characteristic of oligosaccharides that are coupled to glycoproteins or to other compounds according to the methods described herein, wherein the oligosaccharides contain at least one M6P group and, in an exemplary embodiment, two or more M6P groups.

As used herein, the term "effective" refers to a characteristic of an amount of a compound produced according to the methods of the present invention, wherein the amount of the compound has the effect of preventing or reducing a deficiency of a lysosomal enzyme in a subject. The lysosomal enzyme deficiency is, for example, the result of a genetic mutation in a human that produces a lysosomal storage disease. Such diseases include, for example, Gaucher disease wherein a deficiency of beta-glucocerebrosidase results in the accumulation of glucosylceramide, Fabry disease wherein a deficiency of alpha-galactosidase A results in accumulation of globotriaosylceremide, Pompe disease wherein a deficiency of acid alpha-glucosidase results in accumulation of glycogen alpha 1–4-linked oligosaccharides, and Tay-Sachs disease wherein a deficiency of beta-N-acetyl-hexosaminidase leads to accumulation of GM2 ganglioside, and other diseases including Hurler or Hurler-Scheie disease, Krabbe disease, Metachromatic leukodystrophy, Hunter disease, Sanfilippo A and B disease, Morquip A disease, and Maroteaux-Lamy disease and other diseases (see Holton, J. B., 1994, THE INHERITED METABOLIC DISEASES, $2^{nd}$ Edition; Scriver et al., 1995, THE METABOLIC BASIS OF INHERITED DISEASE, Volume 2, $7^{th}$ Edition, which are herein incorporated by reference).

Thus, in an exemplary embodiment, a method for coupling a highly phosphorylated mannopyranosyl oligosaccharide compound to a glycoprotein having at least one glycan includes derivatizing the highly phosphorylated manopyrosanyl oligosaccharide compound with a chemical compound containing a carbonyl-reactive group; oxidizing the glycoprotein having the at least one glycan to generate at least one aldehyde group on the glycoprotein; and reacting the oxidized glycoprotein with the derivatized highly phosphorylated mannopyranosyl oligosaccharide compound to form a new compound having a hydrazone bond. Oxidizing the glycoprotein having the at least one glycan is accomplished using, for example, periodate or galactose oxidase.

The glycoprotein having the at least one glycan is, for example, a glycoprotein such as a lysosomal enzyme. The glycoprotein can be derived from a variety of sources. In the case of lysosomal enzymes, natural sources include human placenta and other animal tissues. Alternatively, lysosomal enzymes that are especially useful for modification according to the present methods are produced by recombinant protein expression systems, including yeast, mammalian cells, insect cells, plant cells and transgenic animals or plants.

The chemical compound containing the carbonyl-reactive group is any compound that reacts with carbonyl groups to form a hydrazone bond. Suitable such compounds include, for example, hydrazine, hydrazide, aminooxy, and semicarbazide and the like.

In one embodiment, the highly phosphorylated mannopyranosyl oligosaccharide compound contains at least one mannose 6-phosphate group, such as an oligosaccharide of the formula $6\text{-P-M}_n\text{-R}$ wherein:

M is a mannose or mannopyranosyl group;

P is a phosphate group linked to the C-6 position of M;

R comprises a chemical group containing at least one carbonyl-reactive group; and n is an integer from 1–15, wherein if n>1, $M_n$ are linked to one another by alpha (1,2), alpha (1,3), alpha (1,4), or alpha (1,6). Thus, the highly phosphorylated mannopyranosyl oligosaccharide compound includes compounds such as M6P, phosphopentamannose derived from Hansenula holstii O-phosphomannan, and 6-P-M-(alpha 1,2)-M(alpha 1,2)-M.

In an exemplary embodiment, the oligosaccharides are those biantennary and trianternary oligosaccharides that have the formula of $(6\text{-P-M}_x)_m\text{L}_n\text{-R}$ wherein:

M is a mannose or mannopyranosyl group;

L is a mannose or other hexose or other chemical groups;

P is a phosphate group linked to the C-6 position of M;

R comprises a chemical group containing at least one carbonyl-reactive group;

m is an integer from 2–3;

n is an integer from 1–15, wherein if n>1, $L_n$ are linked to one another by alpha (1,2), alpha (1,3), alpha (1,4), or alpha (1,6); and x is an integer from 1–15.

Thus, the highly phosphorylated mannopyranosyl oligosaccharide compound includes biantennary mannopyranosyl oligosaccharide compounds containing bis-M6P and triantennary mannopyranosyl oligosaccharide compounds containing bis-M6P or tri-M6P. An exemplary such compound is 6-P-M(alpha 1,2)-M(alpha 1,3)-

M

6-P-M(alpha 1,2)-M(alpha 1,6)- which has about 100 times higher affinity to the MPRs than the phosphopentamannose and M6P, and about 10 times higher affinity to the MPRs than the bi- or tri-oligosaccharides bearing a terminal M6P (Distler et al. 1991).

Alternatively, the highly phosphorylated mannopyranosyl oligosaccharide compound can be replaced with oligosaccharides containing terminal hexoses, such as a galactose, a mannose, N-acetylglucosamine, or a fucose, which can bind to different carbohydrate-binding receptors other than CI-MPR.

In addition, the methods include the further step of reducing a compound having a hydrazone bond with a reducing agent to form a compound having an imine bond, which is more stable than the hydrazone bond. The reducing agent is, for example, a cyanoborohydride compound.

FIG. 1 is a schematic representation of the conjugation methods. In a first step, the reducing terminal sugar of oligosaccharides is derivatized to glycosylhydrazine (as shown) or other carbonyl-reactive groups (such as hydrazide, semicarbazide, aminooxy, etc). Such oligosaccharides must have one or more phosphate groups attached to the C 6' position(s) on mannopyranosyl groups (M6P). The oligosaccharide derivatives then react with the carbonyl (aldehyde) groups generated in the oxidized carbohydrates on glycoproteins to form covalent bond conjugates. The glycoproteins are oxidized according to at least three possible methods. By a first method, sialic acids on glycans are oxidized with a low concentration of sodium periodate (less than or equal to 10 mM) to generate the required carbonyl groups. A second method is suitable when terminal galactoses exist on the glycans, in which enzymatic oxidation is used. More specifically, gatactose oxidase is used to oxidize the C 6' hydroxyl group on the galactose groups. This second oxidation method should not inactivate the glycoprotein. In an alternative embodiment of the second oxidation method, sialic acid groups on glycoprotein carbohydrates are removed using neuraminidase to expose the terminal galactoses, and then galactose oxidase is used to oxidize the terminal exposed galactoses as described for the first embodiment of the second oxidation method. By a third oxidation method, the hexoses on the glycans are oxidized with relatively high concentrations of sodium periodate, i.e. with sodium periodate having a concentration of greater than about 10 mM and less than about 500 mM, to open the vicinal hydroxyl groups of the sugar ring. This third oxidation method is potentially harmful to certain glycoproteins that are sensitive to oxidation. To protect the glycoproteins from oxidation of amino acids, reductive agents such as beta-mercaptoethanol or cysteine or others are added to the oxidation reaction.

In the examples infra, a natural phosphorylated oligosaccharide, the phosphopentamannose derived by mild acid hydrolysis of O-phosphomannan extracted from yeast Hansenula holstii NRRL Y-2448, was used. This compound has a structure of 6-P-M(alpha 1,3)-M(alpha 1,3)-M(alpha 1,3)-M(alpha 1,2)-M (M. E. Slodki, 57 BIOCHIMICA ET BIOPHYSICA ACTA 525 (1962); R. K. Bretthauer et al., 12(7) BIOCHEMISTRY 1251 (1973); L. A. Parolis et al., 309 CARBOHYDR. RES. 77 (1998)). Since the terminal mannosyl in phosphopentamannose is linked to the penultimate mannosyl group via alpha 1,3 linkage, this compound exhibits about 6 fold less affinity towards the MPRs than the alpha 1,2 linked mannosyl oligosaccharides (J. Distler et al., 32(15) J. BIOL. CHEM. 21687 (1991)). Preferred oligosaccharides for therapeutic purposes will be those having the terminal and penultimate mannosyl groups linked via an alpha 1,2 linkage. A trisaccharide bearing a terminal M6P is better than a bisaccharide bearing terminal M6P, and a bisaccharide bearing terminal M6P is better than M6P alone (J. Distler et al., 32(15) J. BIOL. CHEM. 21687 (1991); H. Tomoda et al., 213 CARBOHYDR. RES. 37 (1991)).

While the examples are done with the natural product of phosphopentamannose derivatized with hydrazine, it will be clear to one skilled in the art that various changes in form and detail can be made without departing from the true scope of the invention. For example, the oligosaccharide compounds useful in the present invention include any oligosaccharides that can be synthesized and derivatized with any chemical group, such as hydrazine, hydrazides, semicarbazide, aminooxy (L. A. Vilaseca et al. 4(6) BIOCONJUG. CHEM. 515 (1993)) groups, etc., that can react with carbonyl groups. Total synthesis of various mannopyranosyl oligosaccharides containing M6P has been reported (O. P. Srivastava and O. Hindsgaul, 155 CARBOHYDR. RES. 57 (1986); O. P. Srivastava and O. Hindsgaul, 52 J. ORG. CHEM. 2869 (1987); O. P. Srivastava and O. Hindsgaui. 161 CARBOHYDR. RES. 195 (1987)).

In addition, numerous biologically active materials are subject to modification according to the present methods to form novel compounds and compositions. Bioactive materials that are modified by the present methods include glycoproteins, especially lysosomal enzymes isolated from natural sources or produced by recombinant technologies. However, other bioactive materials that are modified by the present methods include antiviral drugs and gene-targeting materials. After modification according to the present methods, the bioactive materials are taken up by target cells through receptor-mediated endocytic pathways. The modified materials do not lose their biological activity, and the covalent bonds are stable at neutral pH between 6.5–7.5 for at least few months in solution at 4 C (degrees centigrade), or indefinitely if lyophilized (J. Singh Kralovec et al., 29 CANCER IMMUNOL. IMMUNOTHER. 293 (1989)). Once inside the cells, however, the covalent bonds in conjugated materials are cleaved into component oligosaccharide derivatives and the biologically active materials by the low pH in the cellular endosomes and lysosomes (pH<5.5) within a relatively short period of time (G. R. Braslawsky et al., 33 CANCER IMMUNOL. IMMUNOTHER. 367 (1991)).

In another embodiment of this invention, other sugar residues that have cognate carbohydrate-binding receptor are modified according to the present methods, and oligosaccharide chains on a glycoprotein can be extended. For example, mildly oxidized sialic acid can be extended with mannose or galactose to target the mannose receptor or asialoglycoprotein receptor to achieve tissue or cell-specific targeting.

In another application of this invention, anti-viral drugs are modified with M6P to enhance their therapeutic efficacy. During viral infection, viral entry also occurs through receptor-mediated endocytosis. Once in the endosome, the low pH induces fusion of viral membrane with the endosome membrane and releases the viral content to the cytosol to start the replication cycle. Current anti-viral drugs are mostly lipophilic so they can pass through the cell membrane and reach cytosol to be effective; therefore they are general and not cellular compartment specific. M6P modification according to the present methods is especially suitable for developing hydrophilic, cellular compartment-specific anti-viral drugs. Anti-viral drugs with M6P are taken up by the cells through MPR-mediated endocytosis to concentrate in endosomes where virus entry occurs, thus subjecting early stage viral infection to attack by the antiviral compound before viral replication, resulting in improved therapeutic value. A similar approach of involving coupling of AZT to mannosylated BSA, which can be taken up by the mannose-receptor, has been shown to have higher anti-viral activity than the AZT parental drug (G. Molema et al., 34(3) J. MEDICINAL CHEM. 1137 (1991)).

In another embodiment of this invention, the methods are used to modify oligonucleotides useful in gene therapy targeted to correct point mutation in genes. More specifically, the methods are used to modify RNA-DNA chimeric oligonucleotides that are used to repair one or two base pair alterations in the genome of mammalian cells (E. B. Kmiec, 17 ADV. DRUG DELIVERY REVIEWS 333 (1995); K. Yoon et al., 93 PROC. NATL. ACAD. SCI. 2071 (1996)). Such a strategy has been used, for example, to correct the mutation responsible for sickle cell anemia in vitro (A. Cole-Strauss et al., 273 SCIENCE 1386 (1996)), to mutate the rat factor IX gene and UGT in rat liver in vivo (B. T. Kren et al., 4 NATURE MEDICINE 285 (1998); B. T. Kren et al., 96(18) PROC. NATL. ACAD. SCI. 10349 (1999); P. Bandyopadhyay et al., 274 J. BIOL. CHEM. 10163 (2000)) and to correct dystrophin in mdx mouse muscle (T. A. Rando et al., 97(10) PROC. NATL. ACAD. SCI. 5363 (2000)). A critical step for success with this strategy is to deliver the oligonucleotides to target cells with high efficiency. The percentage of gene conversion correlates with the efficiency of oligonucleotide delivery, which is enhanced by modifying polycations or lipsosome with lactose for the asioloyglycoprotein receptor on liver hepatocytes (Kren et al. 1998, supra; Kren et al. 1999; supra; Bandyopadhyay et al., supra). In contrast, for the mdx mouse dystrophin, only the muscle near the injection site is converted (Rando et al., supra), presumbly because only cells nearby the injection site take up the injected oliogonucleotides. Thus, an efficient and general delivery approach of the oligonucleotides for a variety of target cells in vivo is especially useful for expanding the application of such gene therapies. Accordingly, the methods described herein permit M6P modification to provide improved delivery of oligonucleotides to target cells by enhancing MPR-mediated uptake. MPRs are present on a wide variety of cells in vivo and MPR-mediated endocytic process is as efficient an uptake process as the asialoglycoprotein receptor-mediated endocytosis on hepatocytes in liver. PEI/liposome delivery systems employed for the aforementioned oligonucleotides, or the oligonucleotides can be easily modified with M6P or M6P oligosaccharide derivatives, thus to expand the target cell types in vivo for gene-targeted therapy.

EXAMPLE 1

Synthesis of Phosphopentamannose-Hydrazine Derivatives

Phosphopentamannose was prepared from phosphomanan obtained from Dr. M. E. Slodki, Northern Regional Research Laboratory, U.S. department of agriculture, Peoria, Ill. phosphopentamannose was prepared essentially as described by M. E. Slodki (1962) and has the following structure: 6-P-M(alpha 1,3)-M(alpha 1,3)-M(alpha 1,3)-M (alpha 1,2)-M.

100 mg of lyophilized powder of phosphopentamannose was added into a glass tube, to which 3 ml of anhydrous hydrazine was added. The tube was filled with nitrogen gas, capped with a tight fitting cap, and wrapped with parafilm. The reaction was proceeded at room temperature for 6–18 hours, after which the hydrazine was evaporated under vacuum while the hydrazine was absorbed through a bottle of sulfuric acid. 2 milliliters of toluene was added and removed by a stream of nitrogen gas to get rid of the residual hydrazine (Tolvanen and Gahmberg, 1986, supra; Gahmberg and Tolvanen, 1994, supra). Phosphopentamannosyl-hydrazine (PPMH) was dissolved in 2 ml of water and dialyzed against 4 liters of 10 mM phosphate buffer (pH 7.0) overnight at 4 degree centigrade, after which the sample was collected and lyophilized.

EXAMPLE 2

Coupling of Phosphopentamannose-Hydrazine to Avidin

Oxidation of Avidin:

1 ml of 2.5 mg/ml of avidin (obtained from Sigma or Pierce) were oxidized with 10 mM sodium periodate in 100 mM sodium acetate (pH 5.6) for 30 minutes at 4 degree centigrade in the dark. After which 25 microliters of glycerol were added and the sample was incubated on ice for 15 minutes to consume the excess sodium periodate. Samples were then dialyzed overnight against 100 mM sodium acetate (pH 5.6) at 4 degree centigrade. 0.5 ml of 2.5 mg/ml avidin without periodate oxidation were processed the same way as untreated control. Samples after dialysis were collected and stored at 4 or –20 degree centigrade until use.

Coupling of Phosphopentamannose-Hydrazine to Oxidized Avidin:

200 microliters of untreated or oxidized avidin (2.5 mg/ml) were mixed with 1 mg of phosphopentamannose-hydrazine dissolved in 20 microliters of 100 mM sodium acetate buffer (pH 5.6) and incubated at 37 degree centigrade for 1 hour. The samples were dialyzed against 2 liters of CI-MPR binding buffer (50 mM imidazole, 150 mM NaCl, 1 mM EDTA, 0.5 mM $MgCl_2$, 1 mM beta-glycerol phosphate, 0.025% Triton X-100, pH 7.0) overnight at 4 degree centigrade. Samples were collected after dialysis. 10 microliters of untreated avidin/conjugated, oxidized avidin control without conjugation, oxidized avidin/conjugated samples were boiled in SDS sample buffer and separated on 12% SDS-gel to see if there is any mobility shift. 50 microliters of the samples are subjected to the CI-MPR binding test. The remaining samples are stored at –20 C until use.

Figure 2:
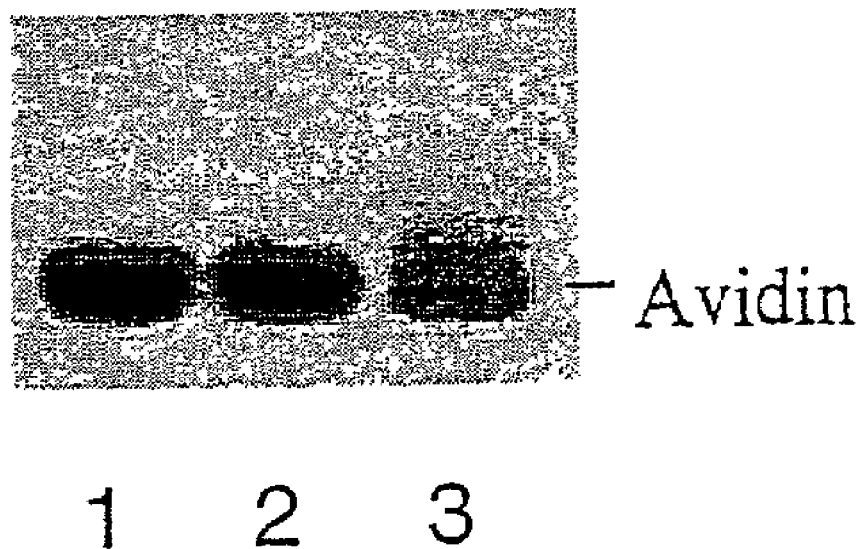
FIG. 2 is a SDS-PAGE analysis of different avidins before and after phosphopentamannose-hydrazine conjugation.

FIG. 2 is a SDS-PAGE analysis of different avidins before and after phosphopentamannose-hydrazine conjugation. Lane 1 shows the results for untreated avidin with conjugation. Lane 2 shows the results for oxidized avidin without conjugation. Lane 3 shows the results for oxidized avidin with phosphopentamannose conjugation. Only Lane 3 shows some avidin retardation in migration, indicating conjugation has occurred. As shown in FIG. 2, there is a clear shift of molecular weight in the oxidized avidin/conjugated sample compare to the untreated avidin/conjugated or oxidized avidin without conjugation controls, indicating that the oxidized avidins are coupled to phosphopentamannose-hydrazine. The molecular weight shift is about 1–4 kDa, suggesting 1–4 phosphopentamannose were coupled to one monomer of avidin.

Binding of unconjugated Avidin and Conjugated Avidin to CI-MPR Column:

100 micrograms of untreated avidin/conjugated (unconjugated) and oxidized avidin/conjugated in 0.5 milliliter CI-MPR binding buffer were passed through a CI-MPR column 5 times, the final passage was collected as flow-through. The column was washed with 8 volumes of binding buffer, an aliquot of the final wash was collected, and finally the bound avidin were eluted with 0.5 milliliter of 5 mM M6P in binding buffer. 20 microliters of the flow through, the final wash and the eluted samples were separated on SDS-gel as described for FIG. 2.

Figure 3:
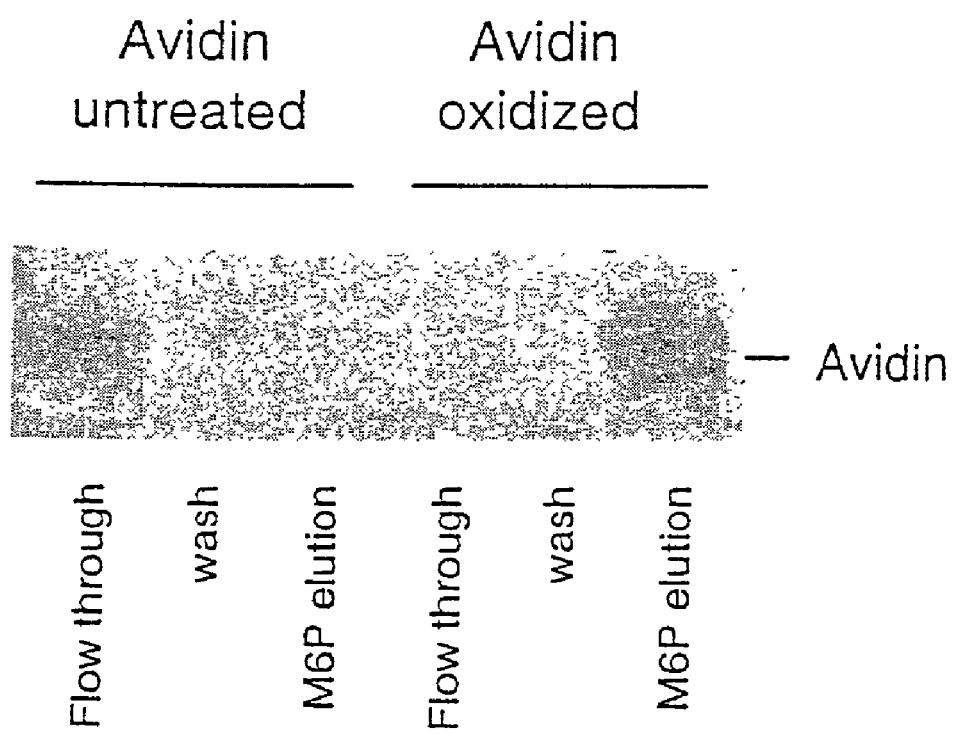
FIG. 3 is a CI-MPR binding analysis of untreated avidin and oxidized avidin conjugated with phosphopentamannose-hydrazine.

FIG. 3 is a CI-MPR binding analysis of untreated avidin and oxidized avidin conjugated with phosphopentamannose-hydrazine. As is shown in FIG. 3, none of the untreated/conjugated avidin binds to the CI-MPR column, whereas all the oxidized avidin/conjugated binds to the CI-MPR column, indicating the efficiency of coupling of phosphopentamannose-hydrazine to oxidized avidin is nearly 100%. The oxidized avidin/unconjugated sample, as the untreated avidin, also does not bind to CI-MPR column (data not shown), indicating the coupling procedure is specific.

EXAMPLE 3

Conjugation of Phosphopentamannose-Hydrazine to Beta-Glucuronidase:

One major concern about the conjugation is that lysosomal enzymes conjugated in such a way must retain enzymatic activity, preferably full activity. While the avidin conjugation result clearly has shown that the coupling process is highly efficient, whether the coupling process affect its biological activity is unknown, in particular, avidin is a stable protein, not an enzyme. Therefore in the following example, lysosomal enzyme beta-glucuronidase isolated from bovine liver (50,000 U/mg, not completely pure, purchased from Sigma) was used.

Oxidation and Coupling Processes do not Inactivate Beta-Glucuronidase:

6 mg of beta-glucuronidase were dissolved in 1.5 ml of water, 1.3 ml of the material (4 mg/ml) were dialyzed against 100 mM NaAc (pH 5.6) overnight at 4 degree centigrade. 200 microliters of the rest sample were kept at 4 degree centigrade as water-control.

Oxidation:

Of the sodium acetate dialyzed beta-glucuronidase, 0.5 ml were kept as untreated-dialyzed material, 0.8 ml were oxidized with 10 mM sodium periodate at 4 degree centigrade for 30 minutes. After which 20 microliters glycerol were added and the sample mixed on ice for 10 minutes to decompose all the excess sodium periodate, then the oxidized material was dialyzed against 1 liter 100 mM sodium acetate overnight. 0.4 ml of the sample was kept at 4 degree centigrade as oxidized-dialyzed control. The other 0.5-ml of sample were used for phosphopentamannose-hydrazine coupling.

Coupling:

3 mg of phosphopentamannose-hydrazine were dissolved in 25 ul of 100 mM NaAc (pH, 5.6) and mixed with 0.5 ml oxidized beta-glucuronidase (4 mg/ml) and incubated at 37° C. for 2 hours, the coupled sample was dialyzed against CI-MPR binding buffer overnight.

Enzymatic Activity of Variously Treated Beta-Glucuronidase:

To 200 microliters of 100 mM p-nitrophenyl beta-glucuronide in 100 mM sodium acetate (pH 5.0), 15 microliters of water as negative control, 15 microliters of beta-glucuronidase dissolved in water, 15 microliters of sodium acetate dialyzed-untreated beta-glucuronidase, 15 microliters of oxidized-dialyzed beta-glucuronidase and 15 microliters of oxidized beta-glucuronidase+phosphopentamannose-hydrazine were added. After incubation at 37 C for 1 hr, 200 microliters of 200 mM glycine (pH 10.4) were added. OD of each sample was measured at 400 nm.

Results:

| Samples | OD400 nm |
| --- | --- |
| 15 microliters water; | 0.00 |
| 15 microliters of beta-glucuronidase dissolved in water; | 1.40 |
| 15 microliters of Untreated NaAc dialyzed beta-glucuronidase; | 1.37 |
| 15 microliters of oxidized beta-glucuronidase NaAc-dialyzed; | 1.43 |
| 15 microliters of beta-glucuronidase oxidized + phosphopentamannose; | 1.44 |

Figure 4:
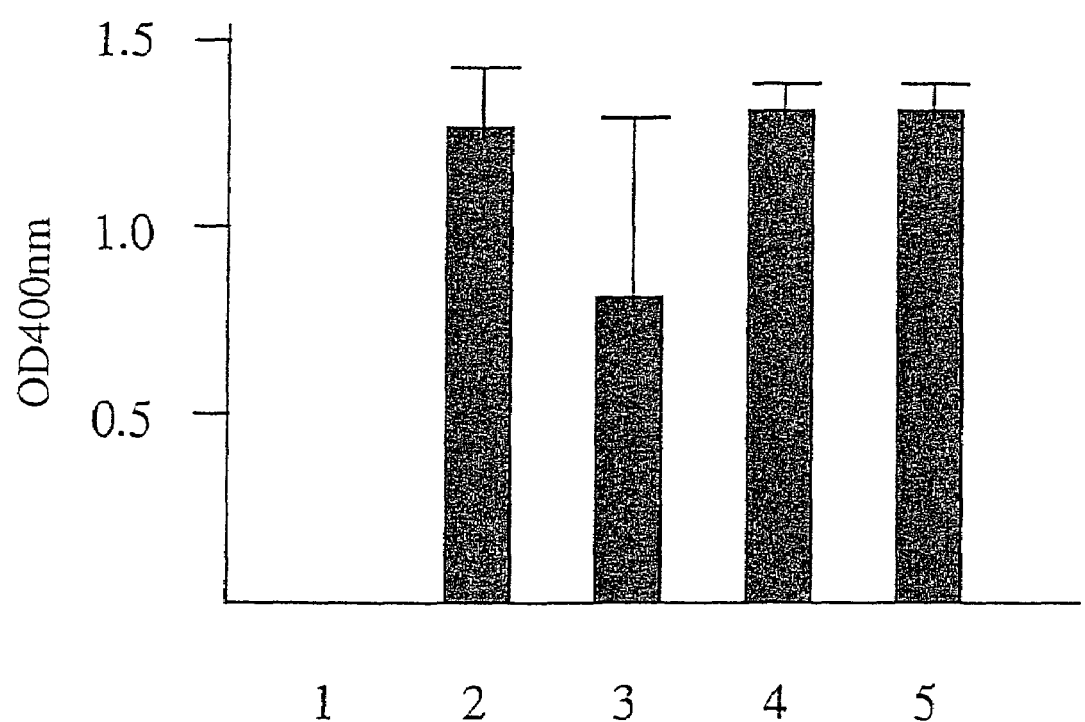
FIG. 4 is a bar graph showing enzymatic activity of beta-glucuronidase after different treatments including after conjugation.

FIG. 4 is a bar graph showing enzymatic activity of beta-glucuronidase after different treatments including after conjugation. 1 is $H_2O$ control; 2, beta-glucuronidase dissolved in $H_2O$; 3, beta-glucuronidase dialyzed against NaAc (pH 5.6); 4, oxidized beta-glucuronidase dialyzed against NaAc, and 5, oxidized beta-glucuronidase conjugated with phospho-pentamannose-hydrazine. The results represent an average of three experiments and indicate nearly equal beta-glucuronidase activity in all samples. Thus, the overall procedure did not appear to inactivate the beta-glucuronidase. This result is expected because the coupling procedure does not involve the protein backbone, and thus should not affect the overall protein conformation.

CI-MPR Binding and Beta-Glucuronidase Assay:

100 microliters of untreated beta-glucuronidase (CI-MPR binding buffer dialyzed) and 100 microliters of oxidized beta-glucuronidase+phosphopentamannose-hydrazine conjugated (CI-MPR binding buffer dialyzed) were mixed with 400 microliters of CI-MPR binding buffer (pH 7.0). 50 microliters of each sample were saved as starting material for late beta-glucuronidase assay.

450 microliters of each sample were passed over a 2 ml CI-MPR column (pre-equlibrated with CI-MPR binding buffer) 5 times. The flow-through of each sample was saved. The column was washed with 8 volumes of CI-MPR binding buffer, the last 0.5 ml was saved as final wash. Finally, the column was eluted with 5 mM M6P in CI-MPR binding buffer by passing over the column 4 times, the eluates were collected as M6P elutions. Therefore each sample has 3 fractions plus the starting material controls.

Beta-Glucuronidase Assay:

To 200 microliters of 100 mM p-nitrophenyl glucuronide in 100 mM sodium acetate buffer (pH 5.0), 30 microliters of water, 30 microliters of untreated beta-glucuronidase column starting material, 30 microliters of untreated beta-glucuronidase flow-through, 30 microliters of untreated beta-glucuronidase wash, 30 microliters of untreated beta-glucuronidase M6P elution, 30 microliters of oxidized beta-glucuronidase+PPMH (imidazole) column starting material, 30 microliters of untreated beta-glucuronidase+PPMH flow-through, 30 microliters of untreated beta-glucuronidase+PPMH wash, 30 microliters of untreated beta-glucuronidase+PPMH M6P elution, were added, the samples were incubated at 37 C for 1 hour. 200 microliters of 200 mM glycine (pH 10.4) were added to each sample to stop the reaction and OD400 nm was measured.

Results:

| Samples | OD400 nm: |
| --- | --- |
| 30 microliters water; | 0.00 |
| 30 microliters of untreated beta-glucuronidase column starting mateial; | 1.43 |
| 30 microliters of untreated beta-glucuronidase flow through; | 1.36 |
| 30 microliters of untreated beta-glucuronidase wash; | 0.00 |
| 30 microliters of untreated beta-glucuronidase M6P elution; | 0.00 |
| 30 microliters of oxidized beta-glucuronidase + PPMH column starting material; | 1.41 |
| 30 microliters of untreated beta-glucuronidase + PPMH flow through; | 0.27 |
| 30 microliters of untreated beta-glucuronidase + PPMH wash; | 0.00 |
| 30 microliters of untreated beta-glucuronidase + PPMH M6P elution; | 0.06 |

Figure 5:
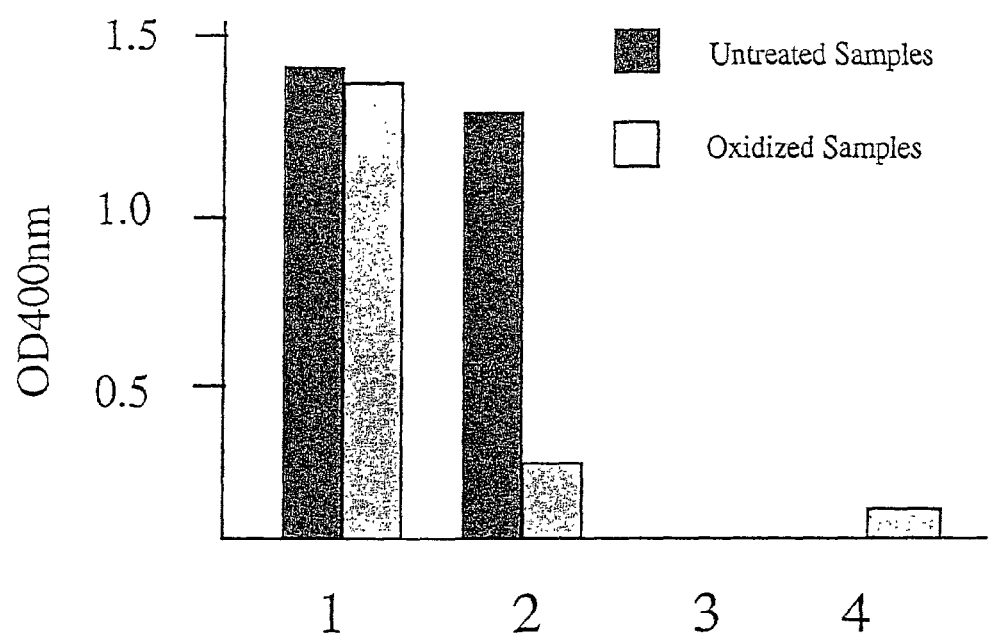
FIG. 5 is a bar graph comparing CI-MPR binding of untreated and oxidized phosphopentamannose-conjugated beta-glucuronidase.

FIG. 5 is a bar graph comparing the CI-MPR binding results for untreated and oxidized phosphopentamannose-conjugated beta-glucuronidase. For the untreated material, nearly 100% of the starting activity was in the flow through, nothing was in the final 0.5 ml wash and M6P elution fractions. However, for the oxidized beta-glucuronidase+phosphopentamannose-hydrazine sample, only 19% of the starting activity was in the flow through, nothing in the final 0.5 ml wash and ~5% was in the M6P elution fraction.

For the untreated sample, the total beta-glucuronidase activities in the starting material and in the flow-through are about equal so there is no clear loss of sample during the column binding. However, for the oxidized/conjugated beta-glucuronidase sample, the total activity of the flow-through and the M6P elution does not add up to the total activity of the starting material. This is not due to the loss of enzymatic activity by oxidation (FIG. 4), but due to the fact that the oxidized beta-glucuronidase conjugated to phosphopentamannose has relatively low binding affinity to CI-MPR (J. Distler et al., supra), especially when one oxidized glycan was conjugated to only one phosphopentamannose-hydrazine due to steric hindrance of the vicinal aldehyde groups. The binding of oligomannosyl phosphate substrates to CI-MPR column has been well characterized (P. Y. Tong et al., 264(14) J. BIOL. CHEM. 1962 (1989); J. Distler et al., supra). The monophosphate form of oligomannosyl substrate binds to CI-MPR column with low-affinity compare to the bisphosphorylated substrate, with large portion of the monophosphate substrate being eluted during the washing step and the rest eluted with M6P, whereas the bisphosphorylated substrate can only be eluted with M6P (P. Y. Tong et al., supra). Therefore, the most likely possibility is that the oxidized beta-glucuronidase conjugated with phosphopentamannose-hydrazine may just behave like the substrate with only one monophosphate and being lost in the first few volumes of washing buffer.

All primary references cited herein are hereby incorporated by reference in their entirety, together with the references contained therein.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

What is claimed is:

1. A method for coupling a oligosaccharide comprising a phosphorylated hexose to a lysosomal enzyme, the method comprising the steps of:
   (a) derivatizing the oligosaccharide comprising a phosphorylated hexose with a compound containing a carbonyl-reactive group;
   (b) oxidizing the lysosomal enzyme to generate at least one carbonyl group on the lysosomal enzyme; and
   (c) reacting the derivatized oligosaccharide with the oxidized lysosomal enzyme,
   thereby coupling the oligosaccharide to the lysosomal enzyme.

2. The method according to claim 1, wherein the phosphate group is linked to a terminal mannose.

3. The method according to claim 1, wherein the phosphate group is linked to a penultimate mannose.

4. The method according to claim 1, wherein the oligosaccharide comprises two or more mannose-6-phosphate (M6P) groups.

5. The method according to claim 1, wherein the oxidizing step is carried out with periodate or galactose oxidase.

6. The method according to claim 1, wherein the lysosomal enzyme is chosen from beta-glucocerebrosidase, alpha-galactosidase A, acid alpha-glucosidase, alpha-N-acetylglucosaminidase, beta-N-acetyl-hexosaminidase, and beta-glucuronidase.

7. The method according to claim 1, wherein the oligosaccharide is chosen from a biantennary mannopyranosyl oligosaccharide and a triantennary mannopyranosyl oligosaccharide.

8. The method according to claim 7, wherein the biantennary mannopyranosyl oligosaccharide comprises bis-M6P.

9. The method according to claim 7, wherein the triantennary mannopyrannosyl oligoscacharide comprises bis-M6P or tri-M6P.

10. The method according to claim 1, wherein the oligosaccharide comprises:

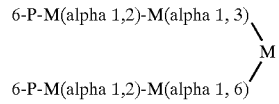

wherein M is mannose or a mannopyranosyl group.

11. The method according to claim 1, wherein the derivatized oligosaccharide has a formula chosen from 6-P-$M_n$-R and (6P-$M_x$)$_m$$L_n$-R,
   wherein M is mannose or a mannopyranosyl group,
   P is a phosphate group linked to the C-6 position of M,
   L is a hexose,
   R is a compound containing at least one carbonyl-reactive group,
   m is an integer ranging from 2 to 3,
   n is an integer ranging from 1 to 15, wherein if n>1, the $M_n$ are linked to one another by alpha (1,2), alpha (1,3), alpha (1,4), or alpha (1, 6), and
   x is an integer ranging from 1 to 15.

12. The method according to claim 11, wherein at least one L is mannose.

13. The method according to claim 11, wherein at least one L is chosen from galactose, N-acetylglucosamine, and fucose.

14. The method according to claim 1 or claim 11, wherein the carbonyl-reactive group is chosen from a hydrazine, a hydrazide, an aminooxy, a semicarbazide.

15. The method according to claim 1, further comprising the step of adding a reducing agent to the coupled lysosomal enzyme.

16. The method according to claim 15, wherein the reducing agent comprises cyanoborohydride.

17. The method of claim 1, wherein the lysosomal enzyme is acid alpha-glucosidase and the carbonyl-reactive group is chosen from a hydrazine, a hydrazide, an aminooxy, a semicarbazide.

18. The method of claim 1, wherein the lysosomal enzyme is acid alpha-glucosidase.

19. The method of claim 1, wherein the carbonyl-reactive group is aminooxy.

* * * * *

UNITED STATES PATENT AND TRADEMARK OFFICE
CERTIFICATE OF CORRECTION

PATENT NO. : 7,001,994 B2
DATED : February 21, 2006
INVENTOR(S) : Yunxiang Zhu

It is certified that error appears in the above-identified patent and that said Letters Patent is hereby corrected as shown below:

<u>Column 15,</u>
Line 16, "coupling a oligosaccharide" should read -- coupling an oligosaccharide --.
Line 17, "hexose" should read -- mannose --.
Lines 19 and 20, "comprising a phosphorylated hexose with a compound containing" should read -- to generate --.

<u>Column 16,</u>
Line 19, "R is a compound containing" should read -- R has --.

Signed and Sealed this

Second Day of May, 2006

JON W. DUDAS
*Director of the United States Patent and Trademark Office*